United States Patent [19]
Lewis et al.

[11] 4,148,794
[45] Apr. 10, 1979

[54] LOWER-ALKYL 3-R₅CO-OCTAHYDRO-2,5-METHANOBENZO[g]QUINOLINE-3-CARBOXYLATES

[75] Inventors: Thomas R. Lewis, Bethlehem; William F. Michne, Poestenkill, both of N.Y.

[73] Assignee: Sterling Drug Inc., New York, N.Y.

[21] Appl. No.: 878,308

[22] Filed: Feb. 16, 1978

Related U.S. Application Data

[60] Continuation-in-part of Ser. No. 818,713, Jul. 25, 1977, Pat. No. 4,119,628, which is a continuation-in-part of Ser. No. 785,746, Apr. 8, 1977, abandoned, which is a division of Ser. No. 725,371, Sep. 22, 1976, abandoned.

[51] Int. Cl.² ............................................. C07D 215/48
[52] U.S. Cl. ....................................... 546/74; 546/43; 546/44; 546/46; 546/39
[58] Field of Search ....................................... 260/287 B

[56] References Cited
PUBLICATIONS

Freed et al., "J. Med. Chem.", (1976), 19(4), pp. 476–480.

*Primary Examiner*—Donald G. Daus
*Assistant Examiner*—David E. Wheeler
*Attorney, Agent, or Firm*—William G. Webb; B. Woodrow Wyatt

[57] ABSTRACT

Lower-alkyl 1-$R_1$-3-$R_5$CO-4a$\alpha$-$R_3$-5$\alpha$-$R_4$-6-$R_2''$-7-$R_2$-8-$R_2'$-9-$R_2'''$-1,2,3,4,4a,5,10,10a-octahydro-2,5-methanobenzo[g]quinoline-3-carboxylates, useful as intermediates for the preparation of 3-$R_1$-6(eq)-$R_4$-7-$R_2''$-8-$R_2$-9-$R_2'$-10-$R_2'''$-11(ax)-$R_3$-11(eq)-$CH_2CH_2COR_5$-1,2,3,4,5,6-hexahydro-2,6-methano-3-benzazocines, useful as analgesics and narcotic antagonists, are prepared by acylation of an appropriate lower-alkyl 1-$R_1$-4a$\alpha$-$R_3$-5$\alpha$C-$R_4$-6-$R_2''$-7-$R_2$-8-$R_2'$-9-$R_2'''$-1,2,3,4,4a,5,10,10a-octahydro-2,5-methanobenzo[g]quinoline-3-carboxylate or carboxylation of an appropriate 1-$R_1$-3-$COR_5''$-4$\alpha$-$R_3$-5$\alpha$-$R_4$-6-$R_2''$-7-$R_2$-8-$R_2'$-9-$R_2'''$-1,2,3,4,4a,5,10,10a-octahydro-2,5-methanobenzo[g]quinoline.

34 Claims, No Drawings

LOWER-ALKYL 3-R₅CO-OCTAHYDRO-2,5-METHANOBENZO[g]QUINOLINE-3-CARBOXYLATES

RELATED APPLICATIONS

This is a continuation-in-part of our prior, copending application Ser. No. 818,713, filed July 25, 1977 now U.S. Pat. No. 4,119,628, which in turn is a continuation-in-part of our prior application Ser. No. 785,746, filed Apr. 8, 1977 and abandoned Aug. 8, 1977, which in turn is a division of our prior application Ser. No. 725,371, filed Sept. 22, 1976 and abandoned Aug. 8, 1977.

BACKGROUND OF THE INVENTION (a) Field of the Invention

This invention relates to lower-alkyl 3-acyl-octahydro-2,5-methanobenzo[g]quinoline-3-carboxylates, useful as intermediates for the preparation of 11(eq)-(2-acylethyl)-hexahydro-2,6-methano-3-benzazocines, which in turn are useful as analgesics and narcotic antagonists.

(b) Description of the Prior Art

Sterling Drug Inc.-owned Japanese Patent Appln. No. 60111/75, filed May 20, 1975, published Dec. 26, 1975, under Provisional Patent Publication No. 160275 describes certain 3-acyl-1,2,3,4,4a,5,10,10a-octahydro-2,5-methanobenzo[g]quinolines useful as intermediates for the preparation of 11(eq)-(2-acylethyl)-1,2,3,4,5,6-hexahydro-2,6-methano-3-benzazocines. Even under the most favorable reaction conditions, however, the prior method produces, as a side product, substantial quantities of 2-substituted-1,2,3,4,4a,5,10,10a-octahydro-3,5-ethenobenzo[g]quinolines, thus appreciably diminishing the yield of the desired product, the hexahydro-2,6-methano-3-benzazocines. Essentially identical disclosure to that in the above-indicated Japanese application is found in Michne U.S. Pat. No. 3,932,422, patented Jan. 13, 1976 on an application filed May 20, 1974.

SUMMARY OF THE INVENTION

In a composition of matter aspect, the present invention relates to certain lower-alkyl 1-R₁-3-R₅CO-4aα-R₃-5α-R₄-6-R₂''-7-R₂-8-R₂'-9-R₂'''-1,2,3,4,4a,5,10,10a-octahydro-2,5-methanobenzo[g]quinoline-3-carboxylates, which are useful as intermediates for the preparation of certain hexahydro-2,6-methano-3-benzazocines.

DETAILED DESCRIPTION INCLUSIVE OF THE PREFERRED EMBODIMENTS

More specifically, this invention provides valuable intermediates having the formula:

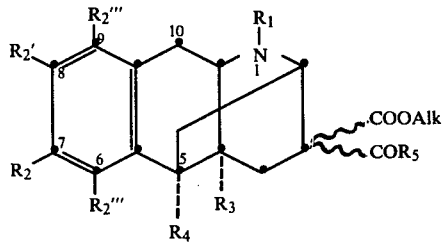

and chemically designated lower-alkyl 1-R₁-3-R₅CO-4aα-R₃-5α-R₄-6-R₂''-7-R₂-8-R₂'-9-R₂'''-1,2,3,4,4a,5,10,10a-octahydro-2,5-methanobenzo[g]quinoline-3-carboxylates, which are useful in the preparation of 3-R₁-6(eq)-R₄-7-R₂''-8-R₂-9-R₂'-10-R₂'''-11(a-x)-R₃-11(eq)-CH₂CH₂COR₅-1,2,3,4,5,6-hexahydro-2,6-methano-3-benzazocines having the formula:

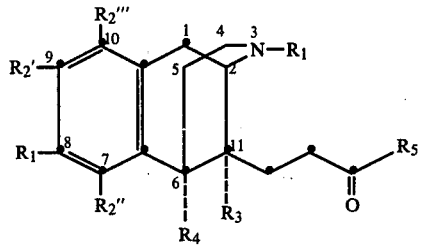

where, in both formulas I and II:

$R_1$ is hydrogen, lower-alkyl, lower-alkenyl, lower-alkynyl, halo-lower-alkenyl, cycloalkyl, cycloalkyl-lower-alkyl, 2- or 3-furylmethyl, or such 2- or 3-furylmethyl substituted on the unsubstituted ring carbon atoms by from one to three methyl groups, phenyl-lower-alkyl, or phenyl-lower-alkyl substituted in the phenyl ring by from one to two members of the group consisting of halogen (including bromine, chlorine and fluorine), lower-alkyl, hydroxy, lower-alkanoyloxy, lower-alkoxy, lower-alkylmercapto, trifluoromethyl, amino, lower-alkanoylamino or a single methylenedioxy attached to adjacent carbon atoms;

$R_2$, $R_2'$, $R_2''$ and $R_2'''$ are each hydrogen, or three of them are hydrogen and the fourth is halogen (including bromine, chlorine or fluorine), lower-alkyl, hydroxy, lower-alkanoyloxy, lower-alkoxy, lower-alkylmercapto, trifluoromethyl, nitro, amino, lower-alkanoylamino, lower-alkoxycarbonylamino or phenyl, or two of the adjacent such groups together are methylenedioxy;

$R_3$ is hydrogen or lower-alkyl;

$R_4$ is hydrogen, lower-alkyl, lower-alkoxy-lower-alkyl, hydroxy-lower-alkyl, lower-alkylthio-lower-alkyl, lower-alkyl-sulfinyl-lower-alkyl, phenylthio-lower-alkyl, phenylsulfinyl-lower-alkyl, lower-alkenyl or halo-lower-alkyl, or $R_3$ and $R_4$ together are divalent lower-alkylene, —$(CH_2)_n$—, where n is one of the integers 3 or 4;

$R_5$ is lower-alkyl, lower-alkylthio-lower-alkyl, lower-alkoxy-lower-alkyl, lower-alkoxy, cycloalkyl, cycloalkyl-lower-alkyl, 2- or 3-furyl, 2- or 3-furyl-$(CH_2)_m$, where m is an integer from 2 to 4, or such 2- or 3-furyl or 2- or 3-furyl-$(CH_2)_m$ substituted on the unsubstituted ring carbon atoms by from one to three methyl groups, phenyl, phenyl-$(CH_2)_m$, or phenyl or phenyl-$(CH_2)_m$ substituted in the phenyl ring by from one to two members of the group consisting of halogen (including bromine, chlorine and fluorine), lower-alkyl, hydroxy, lower-alkanoyloxy, lower-alkoxy, lower-alkylmercapto, trifluoromethyl, amino, lower-alkanoylamino or a single methylenedioxy attached to adjacent carbon atoms; and Alk is lower-alkyl.

As used herein, the terms lower-alkyl or lower-alkoxy mean saturated, acyclic groups which may be straight or branched containing from one to about seven carbon atoms as exemplified by methyl, ethyl, propyl, isopropyl, butyl, nonadjacent t-butyl, methoxy, ethoxy, propoxy, isopropoxy or t-butoxy.

As used herein, the terms lower-alkenyl, halo-lower-alkenyl and lower-alkynyl represent monovalent groups of from three to seven carbon atoms containing one double or triple bond as illustrated, for example, by 1-propenyl, 2-butenyl, 4-pentenyl, 3-methyl-2-butenyl, 1-methyl-2-propenyl, 2-methyl-2-propenyl, 2-propynyl, 2-butynyl, 4-pentynyl, 2-hexynyl and the like. The term halo-lower-alkenyl includes, for example, 3-chloro-2-propenyl, 3-bromo-2-propenyl, 3,3-dichloro-2-propenyl, 3-bromo-2-methyl-2-propenyl and the like.

As used herein, the term cycloalkyl means saturated carbocyclic groups containing from three to seven ring carbon atoms as illustrated, for example, by cyclopropyl, cyclobutyl, cyclopentyl, cyclohexyl, 2-methylcyclobutyl, 4-ethylcyclohexyl and the like.

As used herein, the term lower-alkanoyl means such groups derived from saturated, aliphatic monocarboxylic acids having from one to four carbon atoms, as illustrated, for example, by formyl, acetyl, propionyl, butyryl, isobutyryl and the like.

The above-mentioned Japanese Provisional Patent Publication No. 160,275 describes a process for preparing compounds of formula II which comprises heating a 1-$R_1$-3-$R_5'$CO-4a$\alpha$-$R_3$-5$\alpha$-$R_4$-6-$R_2''$-7-$R_2$-8-$R_2'$-1,2,3,4,4a,5,10,10a-octahydro-2,5-methanobenzo[g]quinoline of formula Ia below with formic acid in an inert organic solvent or with a benzyl-di-lower-alkylammonium formate or a tri-lower-alkylammonium formate. The products of formula IIa are produced by ring opening of the starting material of formula Ia by rupture of the bond indicated by the letter (b). The method however also produces, by rupture of the bond indicated by (a) followed by recyclization of the $R_5'$CO carbonyl group to the nitrogen atom, significant amounts of 1-$R_1$-2-$R_5'$-4a$\alpha$-$R_3$-5$\alpha$-$R_4$-6-$R_2''$-7-$R_2$-8-$R_2'$-1,2,3,4,4a,5,10,10a-octahydro-3,5-ethenobenzo[g]quinolines of formula III, thus diminishing the yield of the main product of formula IIa. The two transformations are represented by the reaction sequence:

di-lower-alkylammonium formate or a tri-lower-alkylammonium formate at a temperature in the range from 120°–150° C. The reaction results in simultaneous ring opening between the 2- and 3-ring carbon atoms of the compounds of formula I and hydrolysis and decarboxylation of the 3-carbo-lower-alkoxy group, COOAlk. Suitable solvents are toluene, xylene or mesitylene. A preferred solvent medium is formic acid in mesitylene.

A further advantage of the use of the $\beta$-keto esters of formula I, rather than the compounds of formula Ia, is that use of the latter requires a reaction time in the order of days, in some cases up to six days, whereas the $\beta$-keto esters of formula I usually require reaction times in the order of minutes or hours, reaction in most cases being complete in four to six hours using formic acid in mesitylene as solvent or in nine to thirteen minutes using trimethylammonium formate at 145° C. In all cases, the course of the reaction is routinely followed by sampling the reaction mixture onto thin layer chromatography plates and noting the disappearance, with increasing reaction time, of zones attributable to starting material.

The compounds of formula I are prepared by either (A) reacting a lower-alkyl 1-$R_1$-4a$\alpha$-$R_3$-5$\alpha$-$R_4$-6-$R_2''$-7-$R_2$-8-$R_2'$-9-$R_2'''$-1,2,3,4,4a,5,10,10a-octahydro-2,5-methanobenzo[g]quinoline-3-carboxylate of formula Ib with an alkali metal amide, for example sodamide or lithium diisopropylamide, in an inert organic solvent and reacting the alkali metal salt thus formed with an appropriate acyl halide, $R_5''$-CO-X, or a lower-alkyl halo formate, X-COO-Alk, or (B) reacting a 1-$R_1$-3-$R_5''$CO-4a$\alpha$-$R_3$-5$\alpha$-$R_4$-6-$R_2''$-7-$R_2$-8-$R_2'$-9-$R_2'''$-1,2,3,4,4a,5,10,10a-octahydro-2,5-methanobenzo[g]quinoline of formula Ic with an alkali metal amide as in

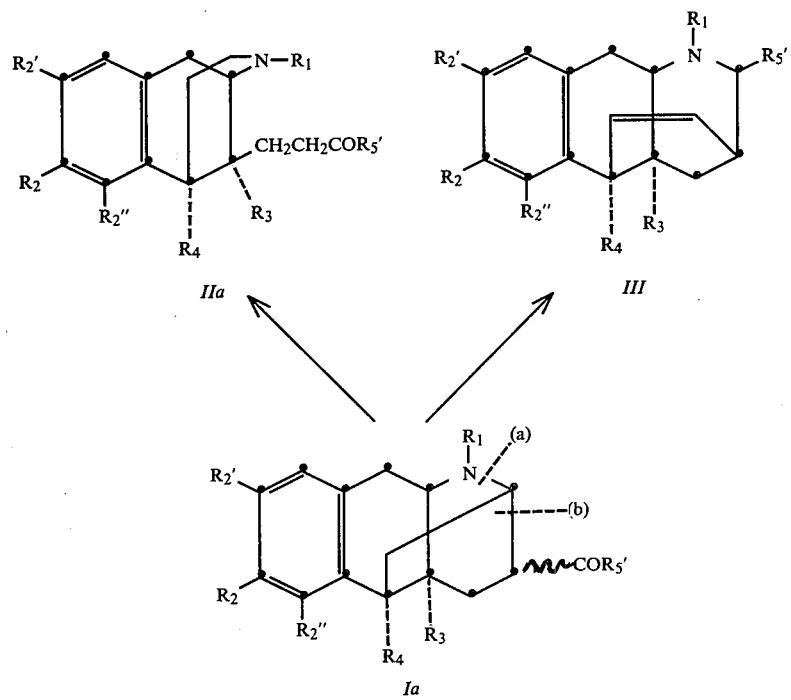

where $R_1$, $R_2$, $R_2'$, $R_2''$, $R_3$ and $R_4$ have the meanings given above, and $R_5'$ is hydrogen, lower-alkyl, phenyl or phenyl-lower-alkyl.

According to the present invention, the compounds of formula II can be produced in high yield, without the formation of side products represented by formula III, by heating the novel $\beta$-keto esters of formula I with formic acid in an inert organic solvent or with a benzylalternative (A) and reacting the resulting alkali metal salt with a lower-alkyl halo formate according to the following reaction sequence:

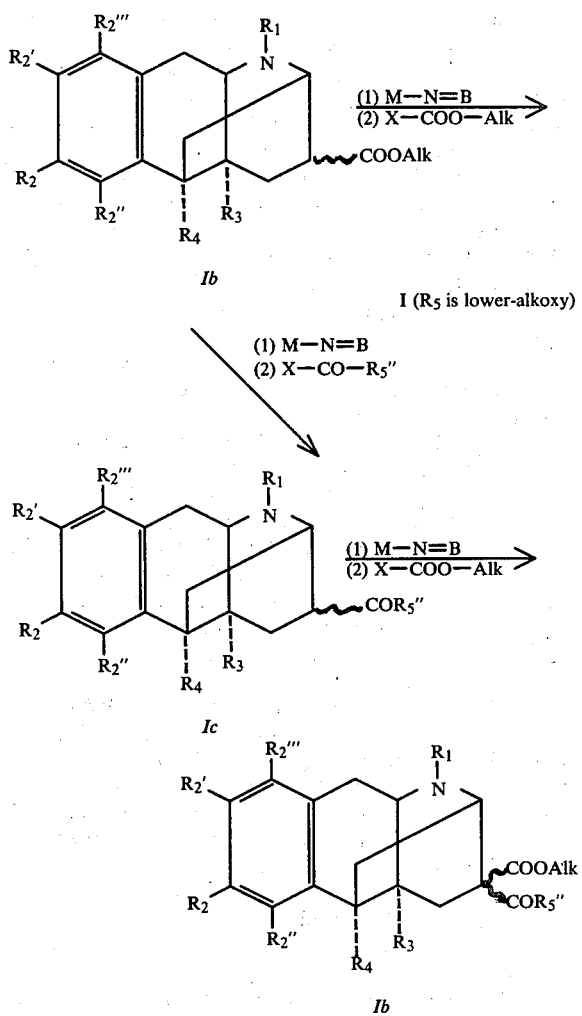

where $R_1$, $R_2$, $R_2'$, $R_2''$, $R_2'''$, $R_3$, $R_4$ and Alk have the meanings given above, $R_5''$ has the same meanings as $R_5$ except it does not represent lower-alkoxy, X is halogen and M—N=B is an alkali metal (M) amide (N=B). The reaction is preferably carried out at a temperature from about −10° C. to about −70° C. Suitable solvents are tetrahydrofuran, diethyl ether or dioxane.

The crude product as obtained from the acylation via either of routes (A) or (B) discussed above generally consists of a mixture of the desired β-keto ester of formula I and unchanged starting material of formulas Ib or Ic (or possibly material epimerized at the 3-position). It has been found that, in the case of the compounds where $R_1$ is lower-alkyl, the β-keto esters of formula I are insoluble in dilute (0.1N) hydrochloric acid, whereas the ester or ketone starting materials of formula Ib and formula Ic, respectively, are readily soluble. This difference in solubilities provides a means of bringing about a clean, and virtually quantitative, separation of the β-keto-ester products from unchanged (or epimerized) starting materials, which involves partitioning the crude product between a water immiscible organic solvent, preferably diethyl ether, and dilute hydrochloric acid. The unchanged starting material of formula Ib or formula Ic is thus dissolved in the acid layer, while the β-keto ester product of formula I is dissolved in the organic layer and can be recovered by evaporation of the organic solution. The unchanged (or epimerized) starting material of formula Ib or formula Ic can be recovered from the aqueous acid solution in a conventional manner and recycled in subsequent runs.

In other cases, where $R_1$ is other than lower-alkyl, for example in the case where $R_1$ is phenyl-lower-alkyl, such separation of the β-keto esters of formula I from unchanged starting material of formulas Ib or Ic is not possible, and in such cases it is necessary to use another technique to separate the desired product from unreacted (and/or epimerized) starting material. This technique requires use of the esters of formula Ib as starting materials and acylation to the β-keto ester of formula I. The crude product from the acylation procedure is then carried directly through, without purification, to the next step involving ring opening to the hexahydro-2,6-methano-3-benzazocine of formula II. The reaction time in the latter reaction is chosen so as to insure complete conversion of all the β-keto ester, i.e. by use of thin layer chromatography analysis, and thus the crude product obtained from the ring opening reaction contains the desired hexahydro-2,6-methano-3-benzazocine of formula II plus any ester of formula Ib which remains unreacted from the acylation step. It is therefore only necessary to warm the crude product with dilute alkali to bring about saponification to the carboxylic acid of any unreacted ester which has been carried through to the final product. The desired hexahydro-2,6-methano-3-benzazocine of formula II can then be extracted out of the alkaline mixture and further purified in a conventional manner as desired, and the unchanged starting material of formula Ib is recovered by neutralization with mineral acid of the aqueous alkaline solution.

The starting materials of formulas Ia, Ib and Ic and methods for their preparation are disclosed in U.S. Pat. No. 3,932,422.

As indicated above, the steric configurations of the 3-carbo-lower-alkoxy group in the compounds of formula Ib, the 3-acyl group (COR$_5''$) in the compounds of formula Ic and of the 3-acyl ($R_5$CO) and 3-carbo-lower-alkoxy groups (COOAlk) in the β-keto esters of formula I are not known with absolute certainty. The esters of formula Ib and the ketones of formulas Ia and Ic disclosed in Japanese Provisional Patent Publication No. 160,275 are disclosed therein as having the β-configuration, i.e. the carbo-lower-alkoxy or the acyl group is cis to the 2,5-methano bridge (vide infra). However, since the time of preparation and filing of the Japanese application, on which that patent publication is based, some uncertainty has developed over whether the ester or acyl groups have the α or the β-configuration. Insofar as the structures of the 2,6-methano-3-benzazocines of formula II (which are prepared from the β-keto esters of formula I) are concerned, the question of the steric configuration at the 3-position of the compounds of formula I is moot, because the asymmetry at the 3-position is destroyed on conversion of the compounds of formula I to the compounds of formula II, and the compounds of formula I having both possible steric configurations at the 3-position are fully operable for the preparation of the compounds of formula II. Suffice it to say that acylation or carboxylation of the compounds of formula Ib or carboxylation of the compounds of formula Ic followed by ring opening and decarboxylation gives, in each case, a single, clean product of formula II.

The compounds of this invention can exist in stereochemically isomeric forms, that is, optical isomers and geometric isomers. If desired, the isolation or the production of a particular stereochemical form can be accomplished by application of general principles known in the prior art. In the nomenclature employed for the compounds of formula II, herein, "ax" stands for axial and "eq" for equatorial, and the configurations are given with reference to the hydroaromatic ring. Thus, the 6(eq), 11(ax) compounds of formula II are in the cis configuration, whereas the 6(eq), 11(eq) compounds are in the trans configuration.

In the nomenclature employed for the compounds of formulas I, Ia, Ib, Ic and III, again configurations are given with reference to the hydroaromatic ring, and the designation "β" indicates the cis configuration relative to the 2,5-methano bridge of the compounds of formula I or the 3,5-etheno bridge of the compounds of formula III. Conversely, the designation "α" indicates the trans configuration relative to the same groups.

The structures of the compounds of this invention were established by the modes of synthesis, by elementary analyses and by infrared and nuclear magnetic resonance spectra. The course of reactions and homogeneity of the products were routinely ascertained by thin layer chromatography.

The manner and process of making and using the invention, and the best mode contemplated of carrying out this invention, will now be described so as to enable any person skilled in the art to which it pertains to make and use the same. The melting points are uncorrected unless noted otherwise.

A. Preparation of Lower-alkyl 3-R₅CO-Octahydro-2,5-methanobenzo[g]quinoline-3-carboxylates of Formula I

1- By acylation of the corresponding lower-alkyl 3-carboxylate

EXAMPLE 1

To a solution of 50 ml. (0.12 mole) of 2.4 N n-butyl lithium in hexane was added, over a period of about thirty minutes while maintaining the temperature at 0° C., a solution of 13.1 g. (0.13 mole) of redistilled diisopropylamine in 110 ml. of dry tetrahydrofuran. The mixture was then cooled to −60° C., and a solution of 34.3 g. (0.1 mole) of ethyl 7-methoxy-1,4aα,5α-trimethyl-1,2,3,4,4a,5,10,10a-octahydro-2,5-methanobenzo[g-]quinoline-3-carboxylate in 110 ml. of tetrahydrofuran was added over a two hour period. The solution was then treated, over a period of about thirty minutes while cooling at −60° C., with a solution of 18.8 g. (0.13 mole) of redistilled hexanoyl chloride in 110 ml. of tetrahydrofuran. The clear reaction mixture was poured into 500 ml. of aqueous sodium bicarbonate, extracted with two 100 ml. portions of ether, and the combined ether extracts were washed once with brine and then dried over sodium sulfate and evaporated to dryness leaving 44 g. of an oil which solidified on standing. The residue was recrystallized from hexane to give 27.5 g. (63%) of ethyl 3-(1-oxohexyl)-7-methoxy-1,4aα,5α-trimethyl-1,2,3,4,4a,5,10,10a-octahydro-2,5-methanobenzo[g]quinoline-3-carboxylate, m.p. 117°–120° C.

Following a procedure similar to that described in Example 1 above, the following compounds of formula I were similarly prepared:

A. Ethyl 7-methoxy-1,4aα,5α-trimethyl-3-(4-methyl-1-oxopentyl)-1,2,3,4,4a,5,10,10a-octahydro-2,5-methanobenzo[g]quinoline-3-carboxylate (22.8 g., 43%, m.p. 97°–100° C. from pentane) prepared by reaction of 40.5 g. (0.12 mole) of ethyl 7-methoxy-1,4aα,5α-trimethyl-1,2,3,4,4a,5,10,10a-octahydro-2,5methanobenzo[g]quinoline-3-carboxylate with 0.13 mole of lithium diisopropylamide followed by reaction of the resulting salt with 17.5 g. (0.13 mole) of 4-methylpentanoyl chloride;

B. Ethyl 7-methoxy-1,5α-dimethyl-3-(1-oxopentyl)-1,2,3,4,4a,5,10,10a-octahydro-2,5-methanobenzo[g-]quinoline-3-carboxylate (5.2 g., 27%, m.p. 87°–92° C., from pentane) prepared by reaction of 15.0 g. (0.046 mole) of ethyl 7-methoxy-1,5α-dimethyl-1,2,3,4,4a,5,10,10a-octahydro-2,5-methanobenzo[g-]quinoline-3-carboxylate with 0.047 mole of lithium diisopropylamide followed by reaction of the resulting salt with 5.7 g. (0.046 mole) of pentanoyl chloride.

Following a procedure similar to that described in Example 1 above, the following compounds of formula I listed in Table 1a were similarly prepared. The melting point and solvent used for crystallization are given in the column headed "m.p. (° C.)/Solv.", and in each instance $R_2'$, $R_2''$ and $R_2'''$ are hydrogen, and Alk is ethyl. Unless noted otherwise, the compounds were isolated as, and the melting points recorded for, the free bases.

Table 1a

| Example | $R_1/R_5$ | $R_2$ | $R_3/R_4$ | % Yield | m.p. (° C.)/Solv. |
|---|---|---|---|---|---|
| 1C | CH₃<br>(CH₂)₂CH₃ | CH₃O | CH₃<br>CH₃ | 62 | 109–111<br>hexane |
| 1D | CH₃<br>CH₂CH(CH₃)₂ | CH₃O | CH₃<br>CH₃ | 44 | 85–88<br>hexane |
| 1E | CH₃<br>CH₂CH₃ | CH₃O | CH₃<br>CH₃ | 53 | 113–115<br>hexane |
| 1F | CH₃<br>CH₃ | CH₃O | H<br>CH₃ | 28 | 120–123<br>ethanol |
| 1G | C₃H₅CH₂<br>(CH₂)₃CH₃ | CH₃O | CH₃<br>CH₃ | 28 | 90–92<br>pentane |
| 1H | CH₃<br>(CH₂)₃SCH₃ | CH₃O | CH₃<br>CH₃ | 59 | 117.5–119<br>hexane |
| 1J | CH₃<br>CH₃ | CH₃O | CH₃<br>CH₃ | 40 | 120–122<br>benzene/hexane |
| 1K | CH₃<br>(CH₂)₄CH₃ | CH₃O | H<br>CH₃ | 39 | 106–108<br>ethanol |
| 1L | CH₃<br>(CH₂)₂C₆H₅ | CH₃O | CH₃<br>CH₃ | 51 | 117–123<br>ethanol |
| 1M | C₆H₅CH₂<br>(CH₂)₄CH₃ | H | CH₃<br>CH₃ | 78 | oil |
| 1N | C₆H₅CH₂<br>CH₃ | CH₃O | CH₃<br>CH₃ | 24 | 123–125<br>hexane |
| 1P | C₆H₅CH₂<br>t-C₄H₉ | CH₃O | CH₃<br>CH₃ | 2 | Oil |

Table 1a-continued

| Example | R₁/R₅ | R₂ | R₃/R₄ | % Yield | m.p. (° C.)/ Solv. |
|---|---|---|---|---|---|
| 1Q | C₆H₅CH₂ (CH₂)₄CH₃ | CH₃O | CH₃ CH₃ | 65 | oil |
| 1R | C₆H₅CH₂ (CH₂)₃CH₃ | CH₃O | CH₃ CH₃ | 37 | oil |
| 1S | C₆H₅CH₂ (CH₂)₅CH₃ | CH₃O | CH₃ CH₃ | 80 | oil |
| 1T | CH₃ (CH₂)₅CH₃ | CH₃O | CH₃ CH₃ | 7 | 86–87 ethanol |
| 1U | C₃H₅CH₂ (CH₂)₃CH₃ | CH₃O | CH₃ CH₃ | 36 | 89–91 pentane |
| 1V | C₆H₅CH₂ (CH₂)₂CH(CH₃)₂ | CH₃O | CH₃ CH₃ | 46 | oil |
| 1W | CH₃ (CH₂)₅CH₃ | CH₃O | H CH₃ | 13 | oil |
| 1X | CH₃ (CH₂)₂CH₃ | CH₃O | H CH₃ | 64 | oil |
| 1Y | CH₃ cyclopentyl(CH₂)₂ | CH₃O | CH₃ CH₃ | 100+(crude) | oil |
| 1Z | CH₃ cyclopropyl(CH₂)₂ | CH₃O | CH₃ CH₃ | 60 | oil |
| 1AA | CH₃ (CH₂)₂CH(CH₃)₂ | CH₃O | H CH₃ | 62 | 90.5-14 93.5 ethanol |
| 1AB | CH₃ (CH₂)₃CH₃ | CH₃O | CH₃ CH₃ | 16 | 93.0–95.5 ethanol |
| 1AC | CH₃ 2-furyl | CH₃O | CH₃ CH₃ | 26 | 142–144 acetone |
| 1AD | CH₃ 2-furyl-(CH₂)₂ | CH₃O | CH₃ CH₃ | 54 | 121–123 hexane |
| 1AE | CH₃ (CH₂)₃CH(CH₃)₂ | CH₃O | CH₃ CH₃ | 37 | 96–100 ethanol |
| 1AF | CH₃ C₆H₅ | CH₃O | CH₃ CH₃ | 1 | 139–141 (a) ethanol/ether |
| 1AG | CH₃ (CH₂)₂CH(CH₃)₂ | CH₃O | CH₃ CH₃ | 43 | oil |
| 1AH | CH₃ (CH₂)₄CH₃ | CH₃O | CH₃ CH₃ | 18 | 98–107 ethanol |
| 1AJ | CH₃ (CH₂)₄CH₃ | H | CH₃ CH₃ | | 121–127 (b) ethanol |
| 1AK | CH₃ (CH₂)₂CH(CH₃)₂ | H | CH₃ CH₃ | | 150–154 (b) ethanol/ether |
| 1AL | CH₃ cyclopentyl(CH₂)₂ | H | CH₃ CH₃ | | 104–132 (b) ethanol/ether |
| 1AM | CH₃ C₆H₅ | H | CH₃ CH₃ | 100 | oil |
| 1AN | CH₃ (CH₂)₂CH(CH₃) | CH₃O | (CH₂)₄ | | |
| 1AP | CH₃ 2-furyl | H | CH₃ CH₃ | 82 | 147–151 ethanol |
| 1AQ | C₃H₅CH₂ (CH₂)₃CH₃ | CH₃O | CH₃ CH₃ | 36 | 89–91 pentane |
| 1AR | CH₃ 4-CH₃C₆H₄ | CH₃O | CH₃ CH₃ | 41 | 143–146 ethanol |
| 1AS | CH₃ 3-CH₃C₆H₄ | CH₃O | CH₃ CH₃ | 58 | 138–141 hexane |
| 1AT | CH₃ cyclobutyl-CH₂ | CH₃O | CH₃ CH₃ | 91 | oil |
| 1AU | CH₃ cyclobutyl-(CH₂)₂ | CH₃O | CH₃ CH₃ | 53 | 121–123 hexane |
| 1AV | CH₃ CH(CH₃)₂ | CH₃O | CH₃ CH₃ | 56 | 118–120 hexane |
| 1AW | CH₃ cyclopentyl | CH₃O | CH₃ CH₃ | 53 | 94–96 pentane |

(a) Ethanesulfonate salt
(b) Picrate salt

It is contemplated that the following lower-alkyl 1-R₁-3-R₅CO-4aα-R₃-5α-R₄-6-R₂'''-7-R₂-8-R₂'-9-R₂'''-1,2,3,4,4a,5,10,10a-octahydro-2,5-methanobenzo[g]quinoline-3-carboxylates of formula I can be prepared from an appropriate lower-alkyl 1-R₁-4aα-R₃-5 α-R₄-6-R₂''-7-R₂-8-R₂'-9-R₂'''-1,2,3,4,4a,5,10,10a-octahydro-2,5-methanobenzo[g]quinoline-3-carboxylate of formula Ib and an appropriate acyl halide R₅''CO—X.

Table 1b (cont,d)

| Example | R₁/R₅ | R₂/R₂' | R₂'/R₂''' | R₃/R₄ | Alk/ |
|---|---|---|---|---|---|
| 1AX | CH₃ cyclohexyl | H H | H H | H CH₂CH₂OCH₃ | C₂H₅ |
| 1AY | CH₃ cyclohexyl-CH₂ | H H | H H | H CH₂CH₂SC₆H₅ | C₂H₅ |
| 1AZ | C₆H₅CH₂ | H | H | CH₃ | C₂H₅ |

Table 1b (cont,d)-continued

| Example | $R_1/R_5$ | $R_2/R_2'$ | $R_2'/R_2'''$ | $R_3/R_4$ | Alk/ |
|---|---|---|---|---|---|
|  | cyclopropyl | H | $CH_3O$ | $CH_3$ |  |
| 1BA | $CH_3$ | H | H | H | $C_2H_5$ |
|  | cyclopropyl-$CH_2$ | H | H | $CH_2CH_2SOC_6H_5$ |  |
| 1BB | $CH_3$ | H | H | H | $C_2H_5$ |
|  | $C_6H_5$ | H | H | $CH=CH_2$ |  |
| 1BC | H | H | H | $CH_3$ | $C_2H_5$ |
|  | 2-Furyl-$(CH_2)_2$ | $CH_3O$ | H | $CH_3$ |  |
| 1BD | H | H | H | $CH_3$ | $C_2H_5$ |
|  | 3-furyl-$(CH_2)_2$ | H | $CH_3O$ | $CH_3$ |  |
| 1BE | $CH_2CH=CH_2$ | H | H | $CH_3$ | $C_2H_5$ |
|  | 5-$CH_3$-3-furyl-$(CH_2)_3$ | H | H | $CH_3$ |  |
| 1BF | $CH_2CH=C(CH_3)_2$ | H | H | $CH_3$ | $C_2H_5$ |
|  | $(CH_2)_4CH_3$ | H | H | $CH_2CH_2OH$ |  |
| 1BG | $CH_2C\equiv CH$ | H | H | $CH_3$ | $C_2H_5$ |
|  | $(CH_2)_4CH_3$ | H | H | $CH_3$ |  |
| 1BH | $C_4H_7CH_2$ | H | H | $CH_3$ | $C_2H_5$ |
|  | $(CH_2)_4CH_3$ | H | H | $CH_3$ |  |
| 1BJ | 3-furyl-$CH_2$ | H | H | $CH_3$ | $C_2H_5$ |
|  | $(CH_2)_4CH_3$ | H | H | $CH_3$ |  |

EXAMPLE 1BK

The preparation of ethyl 7-methoxy-1,4aα,5α-trimethyl-3-(4-methyl-1-oxopentyl)-1,2,3,4,4a,5,10,10a-octahydro-2,5-methanobenzo[g]quinoline-3-carboxylate described above in Example 1A was repeated using 51.5 g. (0.15 mole) of ethyl 7-methoxy-1,4aα,5α-trimethyl-1,2,3,4,4a,5,10,10a-octahydro-2,5-methanobenzo[g]quinoline-3-carboxylate, 0.165 mole of lithium diisopropylamide and 22.2 g. (0.165 mole) of 4-methylpentanoyl chloride in 600 ml. of tetrahydrofuran, but the product was separated from the unreacted starting material by partitioning the crude product between 860 ml. each of diethyl ether and 0.1 N hydrochloric acid. The ether layer was washed with 430 ml. of water which was added to the acid layer, and the combined ether layers were washed with 430 ml. each of saturated sodium bicarbonate and saturated brine. The ether layer, after drying, was taken to dryness in vacuo, and the residue was recrystallized from pentane to give 22.9 g. (0.0519 mole) of the β-keto ester, m.p. 102°-104° C.

The combined aqueous acid solutions remaining from extraction of the ether layer was basified wih 10 ml. of concentrated ammonium hydroxide and extracted several times with a total of 1310 ml. of diethyl ether. The combined ether extracts were washed with 480 ml. each of water and brine, dried and evaporated to dryness to give 16.2 g. of a syrup, which was crystallized from 65 ml. of ethanol to give 12.1 g. (0.035 mole) of recovered starting material, m.p. 97°-98° C. The yield of β-keto ester, based on recovered starting material, is thus 45%.

2-By carboxylation of the corresponding 3-carboxylates or 3-$R_2''$CO ketones

EXAMPLE 2

A solution of 0.055 mole of lithium diisopropylamide in 60 ml. of tetrahydrofuran was prepared from butyl lithium and diisopropylamine using the procedure described in Example 1 above. The solution thus prepared was cooled to −75° C. and treated with a solution of 17.1 g. (0.05 mole) of ethyl 7-methoxy-1,4aα,5α-trimethyl-1,2,3,4,4a,5,10,10a-octahydro-2,5-methanobenzo[g]quinoline-3-carboxylate added over a period of about thirty minutes while maintaining the temperature at −75° C. The solution was then treated dropwise over a period of one hour at −75° C. with a solution of 5.4 g. (0.05 mole) of ethyl chloroformate in 80 ml. of tetrahydrofuran. The mixture was stirred for one hour, then poured into 400 ml. of aqueous sodium bicarbonate and worked up in the same manner as described in Example 1 to give 9.7 g. of crude material which was recrystallized from pentane to give 6.3 g. (30%) of diethyl 7-methoxy-1,4aα,5α-trimethyl-1,2,3,4,4a,5,10,10a-octahydro-2,5-methanobenzo[g]quinoline-3,3-dicarboxylate, m.p. 89°-91° C.

Following a procedure similar to that described in Example 2, using an appropriate 3-$R_5''$CO-1,2,3,4,4a,5,10,10a-octahydro-2,5-methanobenzo[g]quinoline of formula Ic and a lower-alkyl chloroformate in the presence of diisopropylamide, the following compounds of formula I are similarly prepared.

Table 2

| Example | $R_1/R_5$ | $R_2/R_2''$ | $R_2'/R_2''$ | $R_3/R_4$ | Alk |
|---|---|---|---|---|---|
| 2A | $CH_3$ | H | Cl | H | $C_2H_5$ |
|  | $CH_3$ | H | H | $CH_3$ |  |
| 2B | $CH_3$ | H | Br | H | $C_2H_5$ |
|  | $CH_3$ | H | H | $CH_3$ |  |
| 2C | $CH_3$ | H | F | H | $C_2H_5$ |
|  | $CH_3$ | H | H | $CH_3$ |  |
| 2D | $CH_3$ | H | $CF_3$ | H | $C_2H_5$ |
|  | $CH_3$ | H | H | $CH_3$ |  |
| 2E | $CH_3$ | H | $CH_3$ | H | $C_2H_5$ |
|  | $CH_3$ | H | H | $CH_3$ |  |
| 2F | $CH_3$ | $C_6H_5$ | H | H | $C_2H_5$ |
|  | $CH_3$ | H | H | $CH_3$ |  |
| 2G | $CH_3$ | —$OCH_2O$— |  | H | $C_2H_5$ |
|  | $CH_3$ | H | H | $CH_3$ |  |
| 2H | $CH_3$ | H | H | H | $C_2H_5$ |
|  | $CH_3$ | H | H | $CH_2CH_2Cl$ |  |

Table 2-continued

| Example | $R_1/R_5$ | $R_2/R_2''$ | $R_2'/R_2'''$ | $R_3/R_4$ | Alk |
|---|---|---|---|---|---|
| 2J | $CH_3$ | H | H |  | $C_2H_5$ |
|  |  |  |  | $(CH_2)_3$ |  |
|  | $CH_3$ | H | H |  |  |
| 2K | $CH_3$ | H | H |  | $C_2H_5$ |
|  | $CH_3$ |  |  | $(CH_2)_4$ |  |
|  | $CH_3$ | H | H |  |  |
| 2L | cyclohexyl | $CH_3S$ | H | H | $C_2H_5$ |
|  | $CH_3$ | H | H | $CH_3$ |  |
| 2M | $4\text{-}BrC_6H_4CH_2CH_2$ | $CH_3O$ | H | H | $C_2H_5$ |
|  | $CH_3$ | H | H | $CH_3$ |  |
| 2N | $4\text{-}ClC_6H_4CH_2CH_2$ | $CH_3CONH$ | H | H | $C_2H_5$ |
|  | $CH_3$ | H | H | $CH_3$ |  |
| 2P | $4\text{-}FC_6H_4CH_2CH_2$ | $C_2H_5OCONH$ | H | H | $C_2H_5$ |
|  | $CH_3$ | H | H | $CH_3$ |  |
| 2Q | $4\text{-}Cl\text{-}3\text{-}CH_3C_6H_3CH_2CH_2$ | H | H | H | $C_2H_5$ |
|  | $CH_3$ | H | H | $CH_3$ |  |
| 2R | $3\text{-}CH_3COOC_6H_4CH_2CH_2$ | H | H | H | $C_2H_5$ |
|  | $CH_3$ | H | H | $CH_3$ |  |
| 2S | $3,4\text{-}(CH_3O)_2C_6H_3CH_2CH_2$ | H | H | H | $C_2H_5$ |
|  | $CH_3$ | H | H | $CH_3$ |  |
| 2T | $4\text{-}CH_3SC_6H_4CH_2CH_2$ | H | H | H | $C_2H_5$ |
|  | $CH_3$ | H | H | $CH_3$ |  |
| 2U | $3\text{-}CF_3C_6H_4CH_2CH_2$ | H | H | H | $C_2H_5$ |
|  | $CH_3$ | H | H | $CH_3$ |  |
| 2V | $3\text{-}CH_3CONHC_6H_4CH_2CH_2$ | H | H | H | $C_2H_5$ |
|  | $CH_3$ | H | H | $CH_3$ |  |
| 2W | 3,4-$OCH_2OC_6H_3CH_2CH_2$ | H | H | H | $C_2H_5$ |
|  | $CH_3$ |  |  | $CH_3$ |  |
| 2X | $CH_3$ | H | H | H | $C_2H_5$ |
|  | $CH_3$ | H | H | $CH_2CH_2SCH_3$ |  |
| 2Y | $CH_3$ | H | H | H | $C_2H_5$ |
|  | $CH_3$ | $CH_3$ | H | $CH_3$ |  |

B. Conversion of the Compounds of Formula I to 11(eq)-$CH_2CH_2$—$COR_5$-2,6-methano-3-benzazocines of Formula II

EXAMPLE 3

A solution of 10 g. (0.023 mole) of ethyl 3-(1-oxohexyl)-7-methoxy-1,4a$\alpha$,5$\alpha$-trimethyl-1,2,3,4,4a,5,10,10a-octahydro-2,5-methanobenzo[g]quinoline-3-carboxylate in 475 ml. of mesitylene and 35 ml. of 97% formic acid was heated under reflux for seventeen and a half hours. The solvent was removed in vacuo, and the residue was treated with aqueous sodium bicarbonate and ether. The ether extracts were dried over anhydrous magnesium sulfate and then treated with ethereal hydrogen chloride. The material which separated was collected and recrystallized from acetone to give two crops, totalling 6.5 g. (69%), of 8-methoxy-3,6(eq),1-1(ax)-trimethyl-1,2,3,4,5,6-hexahydro-11(eq)-(3-oxooctyl)-2,6-methano-3-benzazocine hydrochloride, m.p. 213°–215° C.

Following a procedure similar to that described in Example 3 above, using an appropriate lower-alkyl 3-$R_5CO$—1,2,3,4,4a,5,10,10a-octahydro-2,5-methanobenzo[g]quinoline-3-carboxylate of formula I in refluxing mesitylene/97% formic acid, the following 1,2,3,4,5,6-hexahydro-11(eq)-$CH_2CH_2COR_5$-2,6-methano-3-benzazocines of formula II were similarly prepared.

A. 8-Methoxy-3,6(eq),11(ax)-trimethyl-1,2,3,4,5,6-hexahydro-11(eq)-(3-oxo-6-methylheptyl)-2,6-methano-3-benzazocine hydrochloride (4.2 g., 38%, m.p. 228°–232° C. from acetone) prepared by refluxing 12 g. (0.027 mole) of ethyl 7-methoxy-1,4a$\alpha$,5$\alpha$-trimethyl-3-(4-methyl-1-oxopentyl)-1,2,3,4,4a,5,10,10a-octahydro-2,5-methanobenzo[g]quinoline-3-carboxylate in a solution of 500 ml. of mesitylene and 35 ml. of 97% formic acid for twenty-one hours and isolating the product in the form of the hydrochloride salt.

Following a procedure similar to that described in Example 3 above the following 1,2,3,4,5,6-hexahydro-11(eq)-$CH_2CH_2COR_5$-2,6-methano-3-benzazocines of formula II were similarly prepared by heating an appropriate lower-alkyl 3-$R_5CO$—octahydro-2,5-methanobenzo[g]quinoline-3-carboxylate in refluxing mesitylene/97% formic acid. The reaction time and % yield are given in the last column. In each instance, $R_2'$, $R_2''$ and $R_2'''$ are hydrogen, and unless noted otherwise, melting points are given for the free bases.

Table 3

| Example | $R_1/R_5$ | $R_2$ | $R_3/R_4$ | m.p. (° C.)/Solv. | Time (Hrs.) % Yield |
|---|---|---|---|---|---|
| 3B | $CH_3$ | $CH_3O$ | H | 182–185 (a) | 24 |
|  | $(CH_2)_3CH_3$ |  | $CH_3$ | acetone | 23 |
| 3C | $CH_3$ | $CH_3O$ | $CH_3$ | 98–99 | 22 |
|  | $(CH_2)_2CH_3$ |  | $CH_3$ | hexane | 70 |
| 3D | $CH_3$ | $CH_3O$ | $CH_3$ | 95–97 | 24 |
|  | $CH_2CH(CH_3)_2$ |  | $CH_3$ | pentane | 60 |

Table 3-continued

| Example | $R_1/R_5$ | $R_2$ | $R_3/R_4$ | m.p. (° C.)/Solv. | Time (Hrs.) % Yield |
|---|---|---|---|---|---|
| 3E | $CH_3$ / $C_2H_5$ | $CH_3O$ | $CH_3$ / $CH_3$ | 100–103 (c) / ethanol | 24 / 63 |
| 3F | $CH_3$ / $CH_3$ | $CH_3O$ | H / $CH_3$ | 175–179 (b) / acetone/ether | 22 / 70 |
| 3G | $C_3H_5CH_2$ / $(CH_2)_3CH_3$ | $CH_3O$ | $CH_3$ / $CH_3$ | 219–220 (b) / acetone/ether | 21 / 67 |
| 3H | $CH_3$ / $(CH_2)_3SCH_3$ | $CH_3O$ | $CH_3$ / $CH_3$ | 140–143 (d) / acetone/ether | 15 / 70 |
| 3J | $CH_3$ / $CH_3$ | $CH_3O$ | $CH_3$ / $CH_3$ | 176–179 (b) / acetone/ether | 19 / 58 |
| 3K | $CH_3$ / $(CH_2)_4CH_3$ | $CH_3O$ | H / $CH_3$ | 127.5–130 (e) / ethanol | 24 / 63 |
| 3L | $CH_3$ / $(CH_2)_2C_6H_5$ | $CH_3O$ | $CH_3$ / $CH_3$ | 176–179 (e) / acetone | 17 / 37 |
| 3M | $C_6H_5CH_2$ / $(CH_2)_4CH_3$ | H | $CH_3$ / $CH_3$ | 190–193 (b) / acetone/ether | 80 / 39 |
| 3N | $C_6H_5CH_2$ / $CH_3$ | $CH_3O$ | $CH_3$ / $CH_3$ | oil | 20.5 / 56 |
| 3P | $C_6H_5CH_2$ / $(CH_2)_4CH_3$ | $CH_3O$ | $CH_3$ / $CH_3$ | 224–227 (b) / acetone/ether | 6.75 / 28 |
| 3Q | $C_6H_5CH_2$ / $(CH_2)_3CH_3$ | $CH_3O$ | $CH_3$ / $CH_3$ | 226–228 (b) / acetone/ether | 20 / 56 |
| 3R | $C_6H_5CH_2$ / $(CH_2)_5CH_3$ | $CH_3O$ | $CH_3$ / $CH_3$ | 219–221 (b) / acetone/ether | 28 / 69 |
| 3S | $CH_3$ / $(CH_2)_5CH_3$ | $CH_3O$ | $CH_3$ / $CH_3$ | 178–182 (b) / ether | 20 / 84 |
| 3T | $C_6H_5CH_2$ / $(CH_2)_2CH(CH_3)_2$ | $CH_3O$ | $CH_3$ / $CH_3$ | 221°–225° C. (b) / acetone/ether | 24 / 36 |
| 3U | $CH_3$ / $(CH_2)_2CH_3$ | $CH_3O$ | H / $CH_3$ | oil | 24 / 67 |
| 3V | $CH_3$ / cyclopentyl$(CH_2)_2$ | $CH_3O$ | $CH_3$ / $CH_3$ | 220–222 (b) / ethanol/ether | 15 / 48 |
| 3W | $CH_3$ / cyclopropyl$(CH_2)_2$ | $CH_3O$ | $CH_3$ / $CH_3$ | 224–225 (b) / ethanol/ether | 24 / 20 |
| 3X | $CH_3$ / $(CH_2)_2CH(CH_3)_2$ | $CH_3O$ | H / $CH_3$ | 131–135 (c) / methanol | 16 / 6 |
| 3Y | $CH_3$ / $(CH_2)_3CH_3$ | $CH_3O$ | $CH_3$ / $CH_3$ | 209–212 (b) / ethanol/ether | 21 / 30 |
| 3Z | $CH_3$ / $(CH_2)_3CH(CH_3)_2$ | $CH_3O$ | $CH_3$ / $CH_3$ | 197–200 (b) / ethanol/ether | 22 / 38 |
| 3AA | $CH_3$ / $C_6H_5$ | $CH_3O$ | $CH_3$ / $CH_3$ | 104–106 / ethanol | 16 / 50 |
| 3AB | $CH_3$ / $(CH_2)_2CH(CH_2)_2$ | $CH_3O$ | $CH_3$ / $C_2H_5$ | 265–267 (b) / ethanol/ether | 16 / 25 |
| 3AC | $CH_3$ / $(CH_2)_4CH_3$ | $CH_3O$ | $CH_3$ / $C_2H_5$ | 225–227.5 (b) / acetone/ether | 16 / 68 |
| 3AD | $CH_3$ / $(CH_2)_4CH_3$ | H | $CH_3$ / $CH_3$ | 191–193 (f) / ethanol/ether | 17 / 30 |
| 3AE | $CH_3$ / $(CH_2)_2CH(CH_3)_2$ | H | $CH_3$ / $CH_3$ | 190–196 (f) / acetone/ether | 16 / 18 |
| 3AF | $CH_3$ / cyclopentyl$(CH_2)_2$ | H | $CH_3$ / $CH_3$ | 234–237 (f) / ethanol/ether | 16 / 39 |
| 3AG | $CH_3$ / $C_6H_5$ | H | $CH_3$ / $CH_3$ | 92–94 / ethanol | 16 / 33 |
| 3AH | $CH_3$ / $(CH_2)CH(CH_3)_2$ | $CH_3O$ | $\|$ $(CH_2)_4$ $\|$ | 169–173 (g) / ethanol/ether | 18 / 25 |
| 3AJ | $CH_3$ / 2-furyl | H | $CH_3$ / $CH_3$ | 96–98 / ethanol | 16 / 9 |
| 3AK | $C_3H_5CH_2$ / $(CH_2)_3CH_3$ | $CH_3O$ | $CH_3$ / $CH_3$ | oil | 13 / 100 |
| 3AL | $CH_3$ / cyclopentyl | $CH_3O$ | $CH_3$ / $CH_3$ | 138–141 (d) / acetone/ether | 15 / 62 |

(a) Picrate salt
(b) Hydrochloride salt
(c) Methanesulfonate melts 215°–220° C.
(d) Methanesulfonate salt
(e) p-Toluenesulfonate salt
(f) Sulfate salt
(g) Hydrochloride hemihydrate

EXAMPLE 4

To a solution of 30 ml. of trimethylammonium formate (prepared by addition of two parts of trimethylamine to five parts of 97% formic acid) heated to 100° C. was added 8.3 g. (0.02 mole) of diethyl 7-methoxy-1,4aα,5α-trimethyl-1,2,3,4,4a,5,10,10a-octahydro-2,5-methanobenzo[g]quinoline-3,3-dicarboxylate (described above in Example 2), and the mixture was heated to boiling for fifteen minutes. The mixture was then poured onto ice, basified with excess sodium hydroxide and extracted with ether. The ether extracts were washed once with brine, dried over magnesium sulfate and taken to dryness to give 6.5 g. of a colorless oil which was recrystallized from hexane to give 3.8 g. (55%) of ethyl 3-[8-methoxy-3,6(eq),11(ax)-trimethyl-1,2,3,4,5,6-hexahydro-2,6-methano-3-benzazocin-11(eq)-yl]propionate, m.p. 91°–93° C.

Following a procedure similar to that described in Example 4 above, using an appropriate lower-alkyl 3-R$_5$CO—1,2,3,4,4a,5,10,10a-octahydro-2,5-methanobenzo[g]quinoline-3-carboxylate of formula I in trimethylammonium formate, the following 1,2,3,4,5,6-hexahydro-11(eq)-CH$_2$CH$_2$COR$_5$-2,6-methano-3-benzazocines of formula II were similarly prepared. The reaction time (in minutes) and percent yield are given in the last column. In each instance, R$_2'$, R$_2''$ and R$_2'''$ are hydrogen; R$_1$, R$_3$ and R$_4$ are methyl; and R$_2$ is methoxy. Unless noted otherwise, melting points are given for the free bases.

Table 4

| Example | R$_5$ | m.p. (° C.)/Solv. | Time (Min.)/ % Yield |
|---|---|---|---|
| 4A | 2-furyl | 119–122 acetone | 12 10 |
| 4B | 2-furyl-(CH$_2$)$_2$ | 144–149 (a) acetone/ether | 10 71 |
| 4C | 4-CH$_3$C$_6$H$_4$ | 87–89 methanol | 15 62 |
| 4D | 3-CH$_3$C$_6$H$_4$ | 94–96 methanol | 14 74 |
| 4E | cyclobutyl-CH$_2$ | 166–168 (a) acetone | 10 64 |
| 4F | cyclobutyl-(CH$_2$)$_2$ | 153–155 (a) acetone/ether | 20 17 |

(a) Methanesulfonate

EXAMPLES 5A–5AT

Following a procedure similar to that described in Example 3 using an appropriate lower-alkyl 3-R$_5$CO-octahydro-2,5-methanobenzo[g]quinoline-3-carboxylate of formula I, it is contemplated that the following 11(eq)—CH$_2$CH$_2$COR$_5$—2,6-methano-3-benzazocines of formula II can be prepared.

Table 5

| Example | R$_1$/R$_5$ | R$_2$/R$_2''$ | R$_2'$/R$_2'''$ | R$_3$/R$_4$ |
|---|---|---|---|---|
| 5A | C$_6$H$_5$CH$_2$ | CH$_3$O | H | CH$_3$ |
|    | t-C$_4$H$_9$ | H | H | CH$_3$ |
| 5B | C$_3$H$_5$CH$_2$ | CH$_3$O | H | CH$_3$ |
|    | (CH$_2$)$_3$CH$_3$ | H | H | CH$_3$ |
| 5C | CH$_3$ | CH$_3$O | H | H |
|    | (CH$_2$)$_5$CH$_3$ | H | H | CH$_3$ |
| 5D | CH$_3$ | H | H | H |
|    | cyclohexyl | H | H | CH$_2$CH$_2$OCH$_3$ |
| 5E | CH$_3$ | H | H | H |
|    | cyclohexyl-CH$_2$ | H | H | CH$_2$CH$_2$SC$_6$H$_5$ |
| 5F | C$_6$H$_5$CH$_2$ | H | H | CH$_3$ |
|    | cyclopropyl | H | CH$_3$O | CH$_3$ |
| 5G | CH$_3$ | H | H | H |
|    | cyclopropyl-CH$_2$ | H | H | CH$_2$CH$_2$SOC$_6$H$_5$ |
| 5H | CH$_3$ | H | H | H |
|    | C$_6$H$_5$ | H | H | CH=CH$_2$ |
| 5J | H | H | H | CH$_3$ |
|    | 2-furyl-(CH$_2$)$_2$ | CH$_3$O | H | CH$_3$ |
| 5K | H | H | H | CH$_3$ |
|    | 3-furyl-(CH$_2$)$_2$ | H | CH$_3$O | CH$_3$ |
| 5L | CH$_2$CH=CH$_2$ | H | H | CH$_3$ |
|    | 5-CH$_3$-3-furyl-(CH$_2$)$_3$ | H | H | CH$_3$ |
| 5M | CH$_2$CH=C(CH$_3$)$_2$ | H | H | CH$_3$ |
|    | (CH$_2$)$_4$CH$_3$ | H | H | CH$_2$CH$_2$OH |
| 5N | CH$_2$C≡CH | H | H | CH$_3$ |
|    | (CH$_2$)$_4$CH$_3$ | H | H | CH$_3$ |
| 5P | C$_4$H$_7$CH$_2$ | H | H | CH$_3$ |
|    | (CH$_2$)$_4$CH$_3$ | H | H | CH$_3$ |
| 5Q | 3-furyl-CH$_2$ | H | H | CH$_3$ |
|    | (CH$_2$)$_4$CH$_3$ | H | H | CH$_3$ |
| 5R | CH$_3$ | H | Cl | H |
|    | CH$_3$ | H | H | CH$_3$ |
| 5S | CH$_3$ | H | Br | H |
|    | CH$_3$ | H | H | CH$_3$ |
| 5T | CH$_3$ | H | F | H |
|    | CH$_3$ | H | H | CH$_3$ |
| 5U | CH$_3$ | H | CF$_3$ | H |
|    | CH$_3$ | H | H | CH$_3$ |
| 5V | CH$_3$ | H | CH$_3$ | H |
|    | CH$_3$ | H | H | CH$_3$ |
| 5W | CH$_3$ | C$_6$H$_5$ | H | H |
|    | CH$_3$ | H | H | CH$_3$ |
| 5X | CH$_3$ | —OCH$_2$O— | H |  |
|    | CH$_3$ | H | H | CH$_3$ |
| 5Y | CH$_3$ | H | H | H |
|    | CH$_3$ | H | H | CH$_2$CH$_2$Cl |
| 5Z | CH$_3$ | H | H | (CH$_2$)$_3$ |
|    | CH$_3$ | H | H | |

Table 5-continued

| Example | R₁/R₅ | R₂/R₂" | R₂'/R₂'" | R₃/R₄ |
|---|---|---|---|---|
| 5AA | CH₃ | H | H | |
| | CH₃ | H | H | (CH₂)₄ |
| 5AB | cyclohexyl | CH₃S | H | H |
| | CH₃ | H | H | CH₃ |
| 5AC | 4-BrC₆H₄CH₂CH₂ | CH₂O | H | H |
| | CH₃ | H | H | CH₃ |
| 5AD | 4-ClC₆H₄CH₂CH₂ | CH₃CONH | H | H |
| | CH₃ | H | H | CH₃ |
| 5AE | 4-FC₆H₄CH₂CH₂ | C₂H₅OCO-NH | H | H |
| | CH₃ | H | H | CH₃ |
| 5AF | 4-Cl-3-CH₃C₆H₃CH₂CH₂ | H | H | H |
| | CH₃ | H | H | CH₃ |
| 5AG | 3-CH₃COOC₆H₄CH₂CH₂ | H | H | H |
| | CH₃ | H | H | CH₃ |
| 5AH | 3,4-(CH₃O)₂C₆H₃CH₂CH₂ | H | H | H |
| | CH₃ | H | H | CH₃ |
| 5AJ | 4-CH₃SC₆H₄CH₂CH₂ | H | H | H |
| | CH₃ | H | H | CH₃ |
| 5AK | 3-CF₃C₆H₄CH₂CH₂ | H | H | H |
| | CH₃ | H | H | CH₃ |
| 5AL | 3-CH₃CONHC₆H₄CH₂CH₂ | H | H | H |
| | CH₃ | H | H | CH₃ |
| 5AM | 3,4-OCH₂OC₆H₃CH₂CH₂ | H | H | H |
| | CH₃ | H | H | CH₃ |
| 5AN | CH₃ | H | H | H |
| | CH₃ | H | H | ·CH₂CH₂SCH₃ |
| 5AP | CH₃ | H | H | H |
| | CH₃ | CH₃ | H | CH₃ |

C. Comparison of Claimed and Prior Methods

The superior overall yield obtained in the instant process for the preparation of 3-benzazocines of formula II in comparison with the process of the prior method disclosed in Japanese Provisional Patent Publication No. 160,275 (and U.S. Pat. No. 3,932,422) is demonstrated by the following descriptions which compare the stepwise and overall yields obtained in the preparation of 8-methoxy-3,6(eq),11(ax)-trimethyl-1,2,3,4,5,6-hexahydro-11(eq)-(3-oxobutyl)-2,6-methano-3-benzazocine via the instant process through the intermediate ethyl 7-methoxy-1,4aα,5α-trimethyl-3-(1-oxoethyl)-1,2,3,4,4a,5,10,10a-octahydro-2,5-methanobenzo[g]quinoline-3-carboxylate of formula I and via the prior art process through the intermediate 7-methoxy-1,4aα,5α-trimethyl-1,2,3,4,4a,5,10,10a-octahydro-2,5-methanobenzo[g]quinoline-3-carboxylic acid and 7-methoxy-1,4aα,5α-trimethyl-3-(1-oxoethyl)-1,2,3,4,4a,5,10,10a-octahydro-2,5-methanobenzo[g]quinoline of formula Ic (R₅" is CH₃) from a common starting material, ethyl 7-methoxy-1,4aα,5α-trimethyl-1,2,3,4,4a,5,10,10a-octahydro-2,5-methanobenzo[g]quinoline-3-carboxylate, of formula Ib. The procedures are illustrated by the reaction sequences:

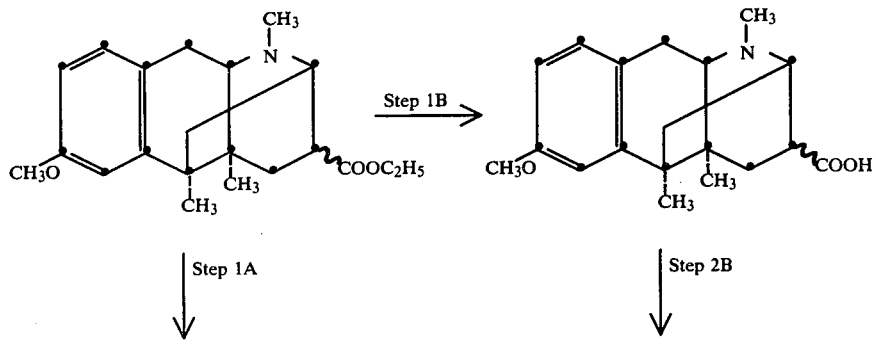

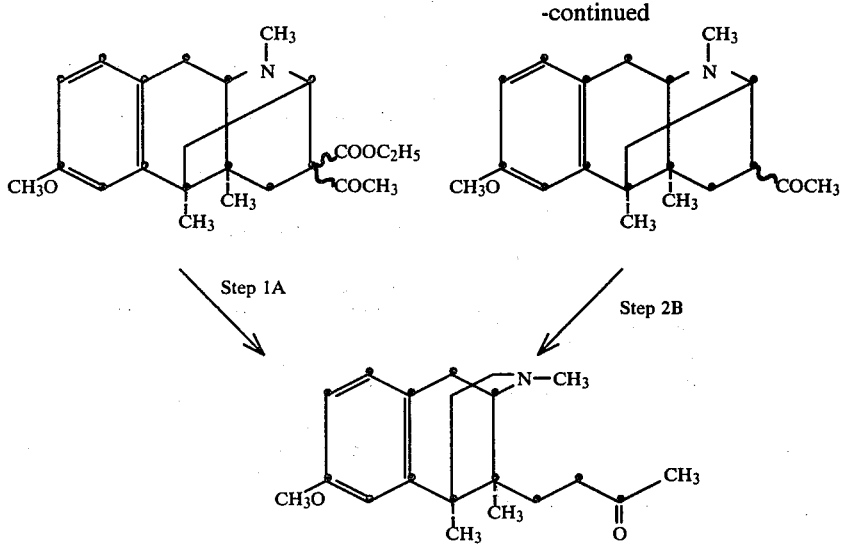

A. The Claimed Process (Step 1A) A solution of 0.127 mole of lithium diisopropylamide in 150 ml. of tetrahydrofuran was prepared using the procedure described above in Example 1. The solution thus prepared was cooled to −70° C. and treated over a period of two hours with stirring with a solution of 40.4 g. (0.118 mole) of ethyl 7-methoxy-1,4aα,5α-trimethyl-1,2,3,4,4a,5,10,10a-octahydro-2,5-methanobenzo[g]quinoline-3-carboxylate in 200 ml. of tetrahydrofuran. When addition was complete, the mixture was stirred for an additional thirty minutes and then treated with stirring over a period of one hour with a solution of 9.9 g. (0.127 mole) of acetyl chloride in 150 ml. of tetrahydrofuran while maintaining the temperature at −70° C. The reaction mixture was then worked up in the manner described above in Example 1, and the crude product recrystallized from hexane to give 18.2 g. (40%) of ethyl 7-methoxy-1,4aα,5α-trimethyl-3-(1-oxoethyl)-1,2,3,4,4a,5,10,10a-octahydro-2,5-methanobenzo[g]quinoline-3-carboxylate, m.p. 120°–123° C.

(Step 2A) A solution of 1.23 g. (0.0032 mole) of the latter in 22 ml. of mesitylene and 81.8 ml. of 97% formic acid was heated under reflux for nineteen hours and then worked up in the manner described above in Example 3. The product was isolated in the form of the free base to give 0.36 g. (36%) of 8-methoxy-3,6(eq),1-1(ax)-trimethyl-1,2,3,4,5,6-hexahydro-11(eq)-(3-oxobutyl)-2,6-methano-3-benzazocine, m.p. 67°–69° C. (14% overall yield from the original starting material).

B. The Prior Process (Step 1B) A solution of 10.0 g. (0.029 mole) of ethyl 7-methoxy-1,4aα,5α-trimethyl-1,2,3,4,4a,5,10,10a-octahydro-2,5-methanobenzo[g]quinoline-3-carboxylate in 100 ml. of ethanol and 50 ml. of water containing 2 g. (0.05 mole) of sodium hydroxide was heated under reflux for about sixteen hours and then concentrated to a small volume. The residue was diluted with about 20 ml. of water, and the pH was adjusted to about 6.5–7.0 with dilute hydrochloric acid. The mixture was diluted with 200 ml. of ethanol, filtered, and the filtrate taken to dryness in vacuo. After drying the residue by repeated concentration from boiling benzene and toluene, the product was crystallized from acetonitrile to give 7.9 g. (>100%) of 7-methoxy-1,4aα,5α-trimethyl-1,2,3,4,4a,5,10,10a-octahydro-2,5-methanobenzo[g]quinoline-3-carboxylic acid, m.p. 118°–121° C.

(Step 2B) A solution of 3.15 g. (0.010 mole) of the latter in 50 ml. of anhydrous tetrahydrofuran was treated dropwise with stirring under a nitrogen atmosphere with 20 ml. (0.020 mole) of a 1.7 molar solution of methyl lithium. The mixture was stirred for about thirty minutes and then poured into a solution containing 10 g. of ammonium chloride in 100 ml. of water. The mixture was extracted twice with ether, the ether extracts dried over magnesium sulfate and taken to dryness to give 1.4 g. of a brown oil which was extracted with boiling pentane to give 0.5 g. (16%) of 7-methoxy-1,4aα,5α-trimethyl-3-(1-oxoethyl)-1,2,3,4,4a,5,10,10a-octahydro-2,5-methanobenzo[g]quinoline. The aqueous layer remaining after extraction of the crude product with ether was saturated with solid sodium hydroxide, and the oil which separated was dissolved in water, acidified strongly and the solid which separated was collected, dried and converted to the hydrochloride salt to give 2.2 g. (0.0062 mole) of the hydrochloride salt (m.p. 295°–297° C.) of the starting carboxylic acid. The corrected yield for the reaction based on the recovered starting material is thus 42%.

(Step 3B) A solution of 1.0 g. (0.0032 mole) of the 7-methoxy-1,4aα,5α-trimethyl-3-(1-oxoethyl)-1,2,3,4,4a,5,10,10a-octahydro-2,5-methanobenzo[g]quinoline obtained in step 2 above was heated in a solution of 22 ml. of mesitylene and 1.8 ml. of formic acid for a total of sixty-seven hours, the course of the reaction being followed from time to time by thin layer chromatography. The reaction mixture was worked up in the manner described above in Example 3 to give 60 mg. (6%) of 8-methoxy-3,6(eq),11(ax)-trimethyl-1,2,3,4,5,6-hexahydro-11(eq)-(3-oxobutyl)-2,6-methano-3-benzazocine, m.p. 62°–65° C. The overall yield from the original starting material was 2.5% based on recovered starting material in step 2.

We claim:
1. A compound having the formula:

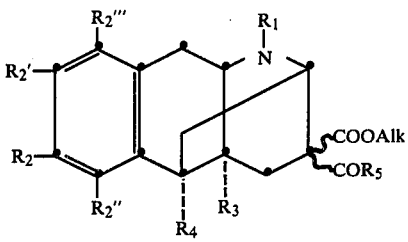

where
R₁ is hydrogen; lower-alkyl; lower-alkenyl; lower-alkynyl; halo-lower-alkenyl; lower-cycloalkyl; lower-cycloalkyl-lower-alkyl; 2- or 3-furylmethyl; or such 2- or 3-furylmethyl substituted on the ring carbon atoms by from one to three methyl groups; phenyl-lower-alkyl; or phenyl-lower-alkyl substituted in the phenyl ring by methylenedioxy or from one to two members of the group consisting of halogen, lower-alkyl, hydroxy, lower-alkanoyloxy, lower-alkoxy, lower-alkylmercapto, trifluoromethyl, amino and lower-alkanoylamino;

R₂, R₂', R₂" and R₂"' are each hydrogen, or three of them are hydrogen and the fourth is halogen, lower-alkyl, hydroxy, lower-alkanoyloxy, lower-alkoxy, lower-alkylmercapto, trifluoromethyl, nitro, amino, lower-alkanoylamino, lower-alkoxycarbonylamino or phenyl, or two of the adjacent such groups together are methylenedioxy;

R₃ is hydrogen or lower-alkyl;

R₄ is hydrogen, lower-alkyl, lower-alkoxy-lower-alkyl, hydroxy-lower-alkyl, lower-alkylthio-lower-alkyl, lower-alkyl-sulfinyl-lower-alkyl, phenylthio-lower-alkyl, phenyl-sulfinyl-lower-alkyl, lower-alkenyl or halo-lower-alkyl, or R₃ and R₄ together are divalent lower-alkylene, —(CH₂)ₙ—, where n is one of the integers 3 or 4;

R₅ is lower-alkyl; lower-alkylthio-lower-alkyl; lower-alkoxy-lower-alkyl; lower-alkoxy; lower-cycloalkyl; lower-cycloalkyl-lower-alkyl; 2- or 3-furyl; 2- or 3-furyl-(CH₂)ₘ, where m is an integer from 2 to 4; or such 2- or 3-furyl or 2- or 3-furyl-(CH₂)ₘ substituted on the unsubstituted ring carbon atoms by from one to three methyl groups; phenyl; phenyl-(CH₂)ₘ; or phenyl or phenyl-(CH₂)ₘ substituted in the phenyl ring by methylenedioxy or from one to two members of the group consisting of halogen, lower-alkyl, hydroxy, lower-alkanoyloxy, lower-alkoxy, lower-alkylmercapto, trifluoromethyl, amino and lower-alkanoylamino; and Alk is lower-alkyl.

2. A compound according to claim 1 where R₁ is lower-alkyl, cycloalkyl-lower-alkyl or phenyl-lower-alkyl; R₂ is lower-alkoxy or hydrogen; R₂', R₂" and R₂"' are each hydrogen; R₃ is hydrogen or lower-alkyl; and R₄ is lower-alkyl, or R₃ and R₄ together are divalent lower-alkylene.

3. A compound according to claim 2 where R₅ is lower-alkyl, lower-alkylthio-lower-alkyl, lower-alkoxy, cycloalkyl, cycloalkyl-lower-alkyl, 2-furyl, 2-furyl-(CH₂)ₘ, phenyl, phenyl-(CH₂)ₘ, or phenyl or phenyl-(CH₂)ₘ substituted in the phenyl ring by from one to three lower-alkyl groups.

4. A compound according to claim 3 where R₅ is lower-alkyl.

5. A compound according to claim 3 where R₅ is lower-alkylthio-lower-alkyl.

6. A compound according to claim 3 where R₅ is phenyl-(CH₂)ₘ.

7. A compound according to claim 3 where R₅ is lower-alkoxy.

8. A compound according to claim 3 where R₅ is 2-furyl.

9. A compound according to claim 3 where R₅ is 2-furyl-(CH₂)ₘ.

10. A compound according to claim 3 where R₅ is cycloalkyl-lower-alkyl.

11. A compound according to claim 3 where R₅ is phenyl or phenyl substituted in the phenyl ring by lower-alkyl.

12. Ethyl 7-methoxy-1,4aα,5α-trimethyl-3-(1-oxohexyl)-1,2,3,4,4a,5,10,10a-octahydro-2,5-methanobenzo[g]quinoline-3-carboxylate according to claim 4.

13. Ethyl 7-methoxy-1,4aα,5α-trimethyl-3-(4-methyl-1-oxopentyl)-1,2,3,4,4a,5,10,10a-octahydro-2,5-methanobenzo[g]quinoline-3-carboxylate according to claim 4.

14. Ethyl 7-methoxy-1,4aα,5α-trimethyl-3-(1-oxobutyl)-1,2,3,4,4a,5,10,10a-octahydro-2,5-methanobenzo[g]quinoline-3-carboxylate according to claim 4.

15. Ethyl 7-methoxy-1,5α-dimethyl-3-(1-oxopentyl)-1,2,3,4,4a,5,10,10a-octahydro-2,5-methanobenzo[g]quinoline-3-carboxylate according to claim 4.

16. Ethyl 7-methoxy-1,4aα,5α-trimethyl-3-(3-methyl-1-oxobutyl)-1,2,3,4,4a,5,10,10a-octahydro-2,5-methanobenzo[g]quinoline-3-carboxylate according to claim 4.

17. Ethyl 7-methoxy-1,4aα,5α-trimethyl-3-(1-oxopropyl)-1,2,3,4,4a,5,10,10a-octahydro-2,5-methanobenzo[g]quinoline-3-carboxylate according to claim 4.

18. Ethyl 7-methoxy-1,5α-dimethyl-3-(1-oxoethyl)-1,2,3,4,4a,5,10,10a-octahydro-2,5-methanobenzo[g]quinoline-3-carboxylate according to claim 4.

19. Ethyl 1-cyclopropylmethyl-7-methoxy-4aα,5α-dimethyl-3-(1-oxopentyl)-1,2,3,4,4a,5,10,10a-octahydro-2,5-methanobenzo[g]quinoline-3-carboxylate according to claim 4.

20. Ethyl 7-methoxy-1,4aα,5α-trimethyl-3-(1-oxoethyl)-1,2,3,4,4a,5,10,10a-octahydro-2,5-methanobenzo[g]quinoline-3-carboxylate according to claim 4.

21. Ethyl 7-methoxy-1,5α-dimethyl-3-(1-oxohexyl)-1,2,3,4,4a,5,10,10a-octahydro-2,5-methanobenzo[g]quinoline-3-carboxylate according to claim 4.

22. Ethyl 7-methoxy-1,4aα,5α-trimethyl-3-(1-oxoheptyl)-1,2,3,4,4a,5,10,10a-octahydro-2,5-methanobenzo[g]quinoline-3-carboxylate according to claim 4.

23. Ethyl 7-methoxy-1,5α-dimethyl-3-(4-methyl-1-oxopentyl)-1,2,3,4,4a,5,10,10a-octahydro-2,5-methanobenzo[g]quinoline-3-carboxylate according to claim 4.

24. Ethyl 7-methoxy-1,4aα,5α-trimethyl-3-(1-oxopentyl)-1,2,3,4,4a,5,10,10a-octahydro-2,5-methanobenzo[g]quinoline-3-carboxylate according to claim 4.

25. Ethyl 7-methoxy-1,4aα,5α-trimethyl-3-[(4-methylthio)-1-oxobutyl]-1,2,3,4,4a,5,10,10a-octahydro-2,5-methanobenzo[g]quinoline-3-carboxylate according to claim 5.

26. Ethyl 7-methoxy-1,4aα,5α-trimethyl-3-(1-oxo-3-phenylpropyl)-1,2,3,4,4a,5,10,10a-octahydro-2,5-methanobenzo[g]quinoline-3-carboxylate according to claim 6.

27. Diethyl 7-methoxy-1,4aα,5α-trimethyl-1,2,3,4,4a,5,10,10a-octahydro-2,5-methanobenzo[g]quinoline-3,3-dicarboxylate according to claim 7.

28. Ethyl 7-methoxy-1,4aα,5α-trimethyl-3-(2-furoyl)-1,2,3,4,4a,5,10,10a-octahydro-2,5-methanobenzo[g]quinoline-3-carboxylate according to claim 8.

29. Ethyl 7-methoxy-1,4aα,5α-trimethyl-3-[3-(2-furyl)-1-oxopropyl]-1,2,3,4,4a,5,10,10a-octahydro-2,5-methanobenzo[g]quinoline-3-carboxylate according to claim 9.

30. Ethyl 7-methoxy-1,4aα,5α-trimethyl-3-(1-oxo-3-cyclopentylpropyl)-1,2,3,4,4a,5,10,10a-octahydro-2,5-methanobenzo[g]quinoline-3-carboxylate according to claim 10.

31. Ethyl 7-methoxy-1,4aα,5α-trimethyl-3-(1-oxo-3-cyclopropyl)-1,2,3,4,4a,5,10,10a-octahydro-2,5-methanobenzo[g]quinoline-3-carboxylate according to claim 10.

32. Ethyl 7-methoxy-1,4aα,5α-trimethyl-3-(1-oxo-3-cyclobutylpropyl)-1,2,3,4,4a,5,10,10a-octahydro-2,5-methanobenzo[g]quinoline-3-carboxylate according to claim 10.

33. Ethyl 7-methoxy-1,4aα,5α-trimethyl-3-(4-methylbenzoyl)-1,2,3,4,4a,5,10,10a-octahydro-2,5-methanobenzo[g]quinoline-3-carboxylate according to claim 11.

34. Ethyl 7-methoxy-1,4aα,5α-trimethyl-3-(3-methylbenzoyl)-1,2,3,4,4a,5,10,10a-octahydro-2,5-methanobenzo[g]quinoline-3-carboxylate according to claim 11.

* * * * *

UNITED STATES PATENT AND TRADEMARK OFFICE
CERTIFICATE OF CORRECTION

PATENT NO. : 4,148,794
DATED : April 10, 1979
INVENTOR(S) : Thomas R. Lewis and William F. Michne It is certified that error appears in the above-identified patent and that said Letters Patent are hereby corrected as shown below:

On the face page, in the Abstract, line 9 thereof, change "5αC" to read --5α--.

On the face page, in the Abstract, line 12 thereof, change "4α" to read --4aα--.

Column 5, line 39, change "Ib" to read --I--.

Signed and Sealed this

Twenth-eighth Day of September 1982

[SEAL]

Attest:

GERALD J. MOSSINGHOFF

Attesting Officer           Commissioner of Patents and Trademarks